(12) United States Patent
Phani Kumar et al.

(10) Patent No.: US 11,817,595 B2
(45) Date of Patent: Nov. 14, 2023

(54) REMOVABLE BATTERY PACK AND LATCH MECHANISM FOR SECURING A REMOVABLE BATTERY PACK

(71) Applicant: Honeywell International Inc., Charlotte, NC (US)

(72) Inventors: Garaga Phani Kumar, Hyderabad (IN); Julius Jancarik, Drasov (CZ); Zoltan Alexi, Brno (CZ)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 232 days.

(21) Appl. No.: 17/336,667

(22) Filed: Jun. 2, 2021

(65) Prior Publication Data
US 2021/0384582 A1 Dec. 9, 2021

(30) Foreign Application Priority Data
Jun. 4, 2020 (IN) .............................. 202011023443

(51) Int. Cl.
*H01M 50/262* (2021.01)
*H01M 10/02* (2006.01)
*A62B 18/00* (2006.01)

(52) U.S. Cl.
CPC ......... *H01M 50/262* (2021.01); *H01M 10/02* (2013.01); *A61M 2205/8206* (2013.01); *A62B 18/006* (2013.01)

(58) Field of Classification Search
CPC ............................ H01M 50/262; H01M 10/02
See application file for complete search history.

(56) References Cited

U.S. PATENT DOCUMENTS

| 4,904,549 | A | | 2/1990 | Goodwin et al. |
| 5,700,042 | A | * | 12/1997 | Weadon .............. H04M 1/0262 292/87 |
| 7,429,430 | B2 | | 9/2008 | Mooty et al. |
| D742,818 | S | | 11/2015 | Lin et al. |

(Continued)

FOREIGN PATENT DOCUMENTS

| EP | 1645705 A1 | 4/2006 |
| EP | 3228288 A1 | 10/2017 |

(Continued)

OTHER PUBLICATIONS

Notice of Allowance received for U.S. Appl. No. 29/736,997, dated Sep. 13, 2021, 7 pages.

(Continued)

*Primary Examiner* — Jane J Rhee
(74) *Attorney, Agent, or Firm* — Alston & Bird LLP (57) ABSTRACT

Apparatuses and systems are disclosed for improved reliability in securing a removable battery pack. An example latch mechanism may include a flexible latch disposed on an outer housing of a removable battery pack, the flexible latch defining an inner surface facing the outer housing and an opposing outer surface, wherein a portion of the opposing outer surface of the flexible latch defines one or more locking tabs that are engageable with one or more engaging slots operatively positioned within a receiving battery enclosure, and wherein the flexible latch is deformable from a first open configuration to a second compressed configuration upon insertion into the battery enclosure.

20 Claims, 11 Drawing Sheets

(56) References Cited

U.S. PATENT DOCUMENTS

| | | |
|---|---|---|
| D790,454 S | 6/2017 | Lee |
| D802,528 S | 11/2017 | Zhang et al. |
| D873,766 S | 1/2020 | Ansehn et al. |
| D908,612 S | 1/2021 | Sexton et al. |
| D922,938 S | 6/2021 | Sexton et al. |
| D922,941 S | 6/2021 | Antonio et al. |
| D928,080 S | 8/2021 | Kim et al. |
| D928,698 S | 8/2021 | Kim et al. |
| 2012/0276428 A1 | 11/2012 | Pendry |

FOREIGN PATENT DOCUMENTS

| | | |
|---|---|---|
| WO | 2009/137770 A2 | 11/2009 |
| WO | 2019/060572 A1 | 3/2019 |

OTHER PUBLICATIONS

Corrected Notice of Allowability (PTTOL-37D) received for U.S. Appl. No. 29/736,997, dated Nov. 18, 2021, 2 pages.

"Battery Pack for Traveler Portable Nebulizer Systems." Direct Home Medical (5 pages), accessed May 27, 2020, retrieved from the internet www.directhomemedical.com/cart/merchant.mvc?screen=PROD&Product_Code=6910d-601-battery-traveler-compressor-nebulizer&Store_Code=DHM&gclid=EAlalQobChMly4H6_MrU6QIVAobICh11xACrEAQYAyABEgIdovD_BwE on Sep. 3, 2021.

gotstogo.com, "Snap Fit Design", [online] retreived from the Internet Apr. 20, 2020, <http://www.gotstogo.com/misc/engineering_info/snap_design.htm>, 7 pages.

Extended European Search Report issued in European Application No. 21177332.0 dated Oct. 25, 2021, 10 pages.

Notice of Allowance received for U.S. Appl. No. 29/736,997, dated Oct. 14, 2021, 2 pages.

EP Office Action dated Jul. 4, 2023 for EP Application No. 21177332, 9 page(s).

\* cited by examiner

REMOVABLE BATTERY PACK AND LATCH MECHANISM FOR SECURING A REMOVABLE BATTERY PACK

CROSS-REFERENCE TO RELATED APPLICATIONS

This application claims priority to Indian Patent Application No. 202011023443, filed Jun. 4, 2020, the content of which is hereby incorporated by reference in its entirety.

TECHNOLOGICAL FIELD

The present application relates generally to removable battery packs, and more particularly, to flexible latches and latch mechanisms for reliably securing a removable battery pack.

BACKGROUND

Powered air-purifying respirators (PAPRs), powered by a removable battery pack, are used to provide breathable air for inhalation by a user in a contaminated environment. Applicant has identified a number of deficiencies and problems associated with conventional apparatuses and systems available for securing a removable battery pack in a PAPR. Through applied effort, ingenuity, and innovation, many of the battery pack securement issues identified have been solved by developing solutions that are included in embodiments of the present disclosure, many examples of which are described in detail herein.

BRIEF SUMMARY

Systems and apparatuses are disclosed herein for improved reliability in securing a removable battery pack in a battery enclosure of a PAPR. With reference to an example latch mechanism, the latch mechanism may include a flexible latch disposed on an outer housing of the removable battery pack, the flexible latch defining an inner surface facing the outer housing and an opposing outer surface, wherein a portion of the opposing outer surface of the flexible latch defines one or more locking tabs that are engageable with one or more engaging slots operatively positioned within the battery enclosure, and wherein the flexible latch is deformable from a first open configuration to a second compressed configuration upon insertion into the battery enclosure.

In some embodiments, the one or more locking tabs protrude outwardly from the opposing outer surface of the flexible latch.

In certain embodiments, the flexible latch further defines a proximal end and a distal end, the proximal end disposed proximate to and extending from the outer housing of the removable battery pack such that the proximal end defines a latch base. In still further embodiments, the one or more locking tabs are disposed proximate to the distal end of the flexible latch. In some embodiments, the flexible latch comprises an arcuate portion proximate to the latch base.

In some embodiments, the flexible latch extends from the outer housing at a first angle in relation to the outer housing, the first angle defining the first open configuration. In certain embodiments, the first angle is an acute angle. In still further embodiments, the flexible latch extends from the outer housing at a second angle in relation to the outer housing, wherein the first and second angles are different and the second angle defines the second compressed configuration.

In some embodiments, the flexible latch is configured to exert an outwardly directed pressure in the second compressed configuration.

In some embodiments, the flexible latch is integrally formed with at least a portion of the outer housing of the removable battery pack. In certain embodiments, the flexible latch is formed during injection molding of at least a bottom portion of the outer housing of the removable battery pack.

In some embodiments, the flexible latch is formed of a polymer material. In certain embodiments, the flexible latch is formed of a polycarbonate/acrylonitrile butadiene styrene blend.

In some embodiments, the one or more locking tabs each have a first edge extending at an acute angle from the outer surface of the flexible latch and a second, opposing edge extending perpendicularly from the outer surface of the flexible latch. In certain embodiments, at least one of the one or more locking tabs has a locking edge, such that engagement of the locking tab with the one or more engaging slots prevents disengagement of the removable battery pack from the battery enclosure.

In some embodiments, the flexible latch is operable to return to the first open configuration upon withdrawal from the battery enclosure.

In some embodiments, the flexible latch is deformable from the second compressed configuration to a third compressed position. In still further embodiments, the flexible latch is operable to deform from the second compressed configuration to the third compressed position upon application of a force sufficient to disengage the one or more locking tabs from the one or more engaging slots of the PAPR.

In some embodiments, the outer housing of the removable battery pack comprises a stopper projection operatively positioned to prevent the flexible latch from overextension.

Other embodiments are directed to a removable battery pack. In some embodiments, the removable battery pack comprises a battery assembly; an outer housing; and a flexible latch, the flexible latch comprising a main body operable to deform from a first open configuration to a second compressed configuration upon insertion into a corresponding battery compartment, a latch base defined by a first end of the main body, the latch base operable to attach the main body of the flexible latch to the outer housing of the removable battery pack, and a latch end comprising one or more locking tabs, the one or more locking tabs operable to engage with one or more engaging slots operatively positioned within the corresponding battery compartment, wherein an angle θ is defined at least in part by an axis of the flexible latch, the angle θ varying in response to application of pressure to the flexible latch.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below. Other features, aspects, and advantages of the subject matter will become apparent from the description, the drawings, and the claims.

BRIEF DESCRIPTION OF THE DRAWINGS

Having described certain example embodiments of the present disclosure in general terms above, non-limiting and non-exhaustive embodiments of the subject disclosure will now be described with reference to the accompanying drawings which are not necessarily drawn to scale. The components illustrated in the accompanying drawings may or may not be present in certain embodiments described herein. Some embodiments may include fewer (or more) components than those shown in the drawings.

DETAILED DESCRIPTION

Definitions

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the terms "example," "exemplary," and the like are used to "serving as an example, instance, or illustration." Any implementation, aspect, or design described herein as "example" or "exemplary" is not necessarily to be construed as preferred or advantageous over other implementations, aspects, or designs. Rather, use of the terms "example," "exemplary," and the like are intended to present concepts in a concrete fashion.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Overview

Powered air-purifying respirators (PAPRs) are self-contained apparatuses commonly used in commercial, industrial, and healthcare settings to provide breathable air for inhalation by users and to prevent users from inhaling harmful substances (e.g., toxic gases, airborne fluids, suspended particulates, etc.) in a contaminated environment. A PAPR typically comprises a blower driven by an electric motor that draws air from the environment through a filter and provides filtered, breathable air to the user. PAPRs typically are powered by a removable battery pack. Such PAPRs are often subjected to extended use and wear requiring the user to be able to exchange the removable battery pack quickly and conveniently. Such PAPRs are also often subjected to impact forces during normal operating use in such commercial, industrial, and healthcare settings. Indeed, PAPRs and battery packs constructed using conventional apparatuses and systems to secure a battery pack in a PAPR have been known to suddenly disengage and come out of the battery enclosure of the PAPR during operation, posing a significant safety concern to the user who may not be provided enough air to breathe while in a contaminated environment. Thus, it is desirable, in some examples, for a PAPR utilized in such environments to support convenient removal and replacement of the battery pack while also reliably securing the removable battery pack during use.

Various embodiments of the present disclosure are directed to an improved latch mechanism, removable battery pack, apparatuses, and systems for improved reliability in securing a removable battery pack in a battery enclosure of a PAPR or other electrical device while also providing for convenient removal and replacement of the battery pack when desired. According to one example embodiment, a latch mechanism may include a flexible latch disposed on an outer housing of the removable battery pack, the flexible latch defining an inner surface facing the outer housing and an opposing outer surface, wherein a portion of the opposing outer surface of the flexible latch defines one or more locking tabs that are engageable with one or more engaging slots operatively positioned within the battery enclosure, and wherein the flexible latch is deformable from a first open configuration to a second compressed configuration upon insertion into the battery enclosure. Accordingly, in some examples, the latch mechanism of the removable battery pack reliably secures the removable battery pack within the battery enclosure of the PAPR via multiple securement features for reliability, but within an integral, one piece latch mechanism, thereby affording more reliability and cost savings as compared to current battery packs.

One or more embodiments of the present disclosure will now be more fully described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details. It should be understood that some, but not all embodiments are shown and described herein. Indeed, the embodiments may be embodied in many different forms, and accordingly this disclosure should not be construed as limited to the embodiments set forth herein. Rather, these embodiments are provided so that this disclosure will satisfy applicable legal requirements. As used herein, the description may refer to a latch mechanism as an example "apparatus." However, elements of the apparatus described herein may be equally applicable to the claimed removable battery pack. Thus, use of any such terms should not be taken to limit the spirit and scope of embodiments of the present disclosure.

Applicant has developed a latch mechanism and removable battery pack that provides reliable and quick securement and withdrawal of a removable battery pack within a battery enclosure. The latch mechanism may prevent or reduce the chance of the removable battery pack from disengaging during normal operating usage. Normal operating usage may include being subjected to extended wear and/or one or more impact forces during use.

Figure 1:
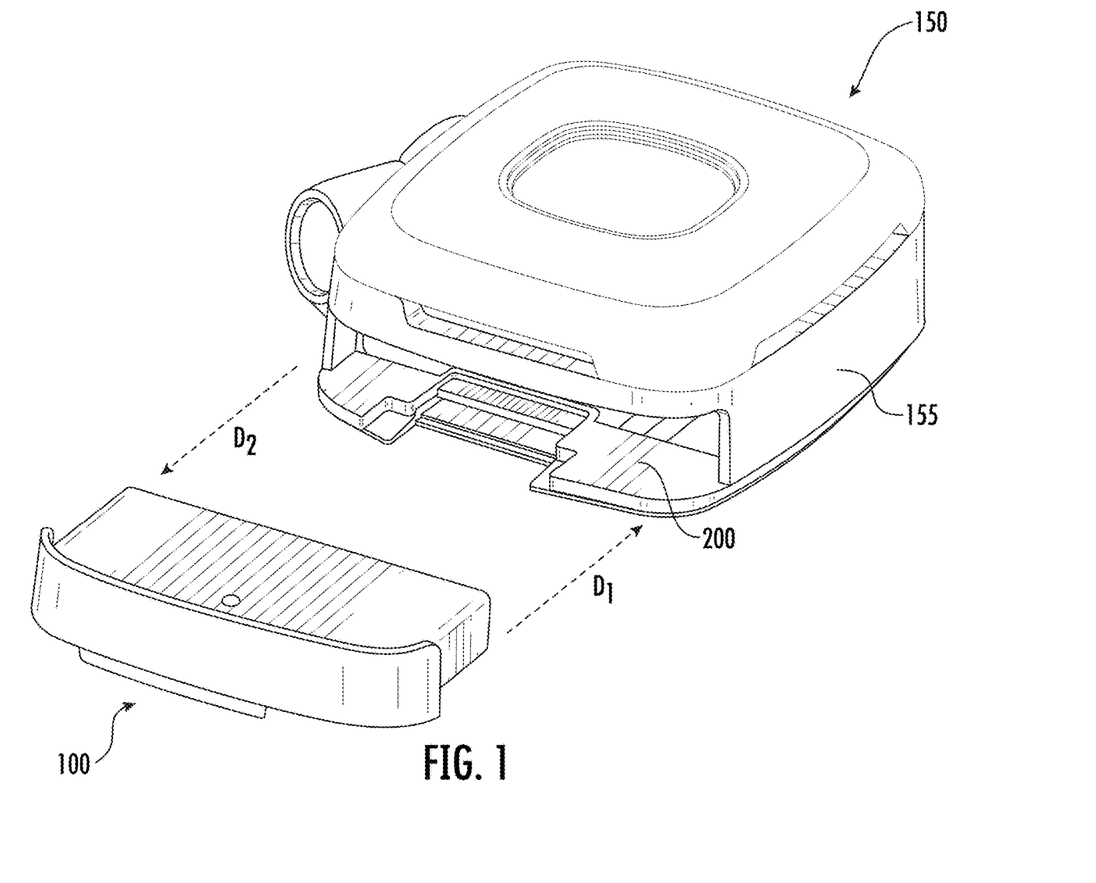
FIG. 1 illustrates a top front perspective view of a PAPR and an example removable battery pack in accordance various aspects and embodiments of the subject disclosure described herein.

With reference to FIG. 1, a top front perspective view of a PAPR 150 and an example removable battery pack 100 are illustrated in accordance with various aspects and embodiments of the subject disclosure described herein. The PAPR 150 has a main body 155 which may house various components, such as a blower motor (not shown), a filter (not shown), and an air pump or fan assembly (not shown), and be configured to draw in air from the environment and provide filtered, breathable air to the user. In use, the PAPR 150 may be operably connected via a hose or other connecting means to a breathing apparatus (e.g., a face mask, a hood, or a full body suit) to supply the filtered, breathable air to the user. The main body 155 of the PAPR comprises a battery enclosure or compartment 200 within which the removable battery pack 100 may be inserted and secured to supply power to the PAPR 150. As depicted in FIG. 1, in an example embodiment, a user pushes a removable battery pack 100 in direction $D_1$ to insert the removable battery pack 100 into the battery enclosure or compartment 200 of the PAPR 150. In another example embodiment, when necessary to remove the removable battery pack 100, the user depresses a flexible latch while pulling the removable battery pack 100 in direction $D_2$ to withdraw the removable battery pack 100 from the battery enclosure or compartment 200.

Figure 2:
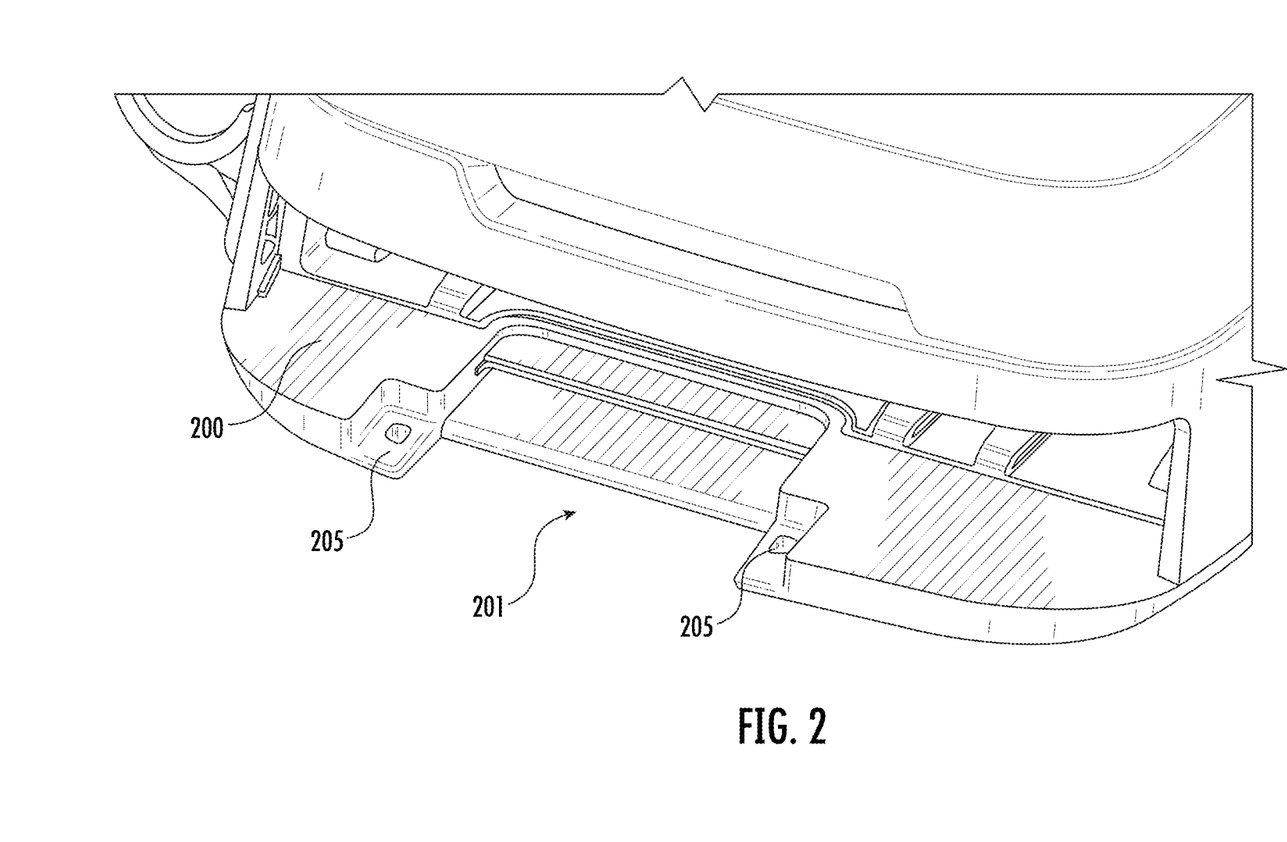
FIG. 2 is an enlarged view of a portion of FIG. 1, illustrating an example battery enclosure with engaging slots in accordance with various aspects and embodiments of the subject disclosure described herein.

With reference to FIG. 2, the battery enclosure or compartment 200 is defined by the main body 155 of the PAPR 150 as an opening or cavity in which the removable battery pack 100 may be inserted to, secured in, and/or removed from the PAPR 150. The battery enclosure or compartment 200 is cooperatively designed to receive a removable battery pack 100 in accordance with various embodiments described herein. In some embodiments, the battery enclosure or compartment 200 may define a latch-receiving void or cutout 201 corresponding to at least a portion of the flexible latch protruding from the removable battery pack 100 (e.g., the distal end of the flexible latch in FIG. 3C). As depicted in FIG. 2, in some embodiments, the latch-receiving void or cutout 201 is disposed proximate to the center of the bottom, forward side of the opening of the battery enclosure 200. In an instance where the removable battery pack 100 is inserted completely and secured within the battery enclosure or compartment 200, such latch-receiving void or cutout 201 may be operable to provide a user access to at least the distal end of the flexible latch in order to depress the flexible latch and withdraw the removable battery pack 100 from the battery enclosure or compartment 200.

With continued reference to FIG. 2, in some embodiments, the battery enclosure or compartment 200 may define one or more engaging slots 205 operatively positioned within the battery enclosure 200 for receiving one or more locking tabs of the flexible latch of the removable battery, as described in detail below with respect to FIG. 3A. As depicted in FIG. 2, in some embodiments, the one or more engaging slots 205 may be positioned on the bottom, forward side, proximate to the opening, of the battery enclosure or compartment 200 in order to receive the one or more locking tabs of the flexible latch, further aiding in reliably securing the removable battery pack 100 within the battery enclosure or compartment 200. It should be appreciated that while illustrated as positioned on the bottom side, proximate to the opening, of the battery enclosure 200, the present disclosure contemplates that the one or more engaging slots 205 may be disposed in any suitable position in the battery enclosure 200 that corresponds to and operatively engages with the one or more locking tabs disposed on a flexible latch of a removable battery pack 100. As described in detail below with respect to FIG. 4, a receiving connection (not shown) may be disposed within the internal opening or cavity of the battery enclosure or compartment 200 corresponding to, and electrically connecting with, a power connection of the removable battery pack 100, thereby creating an electrical connection between the removable battery pack 100 and PAPR 150 to provide power to the PAPR 150.

Figure 3A:
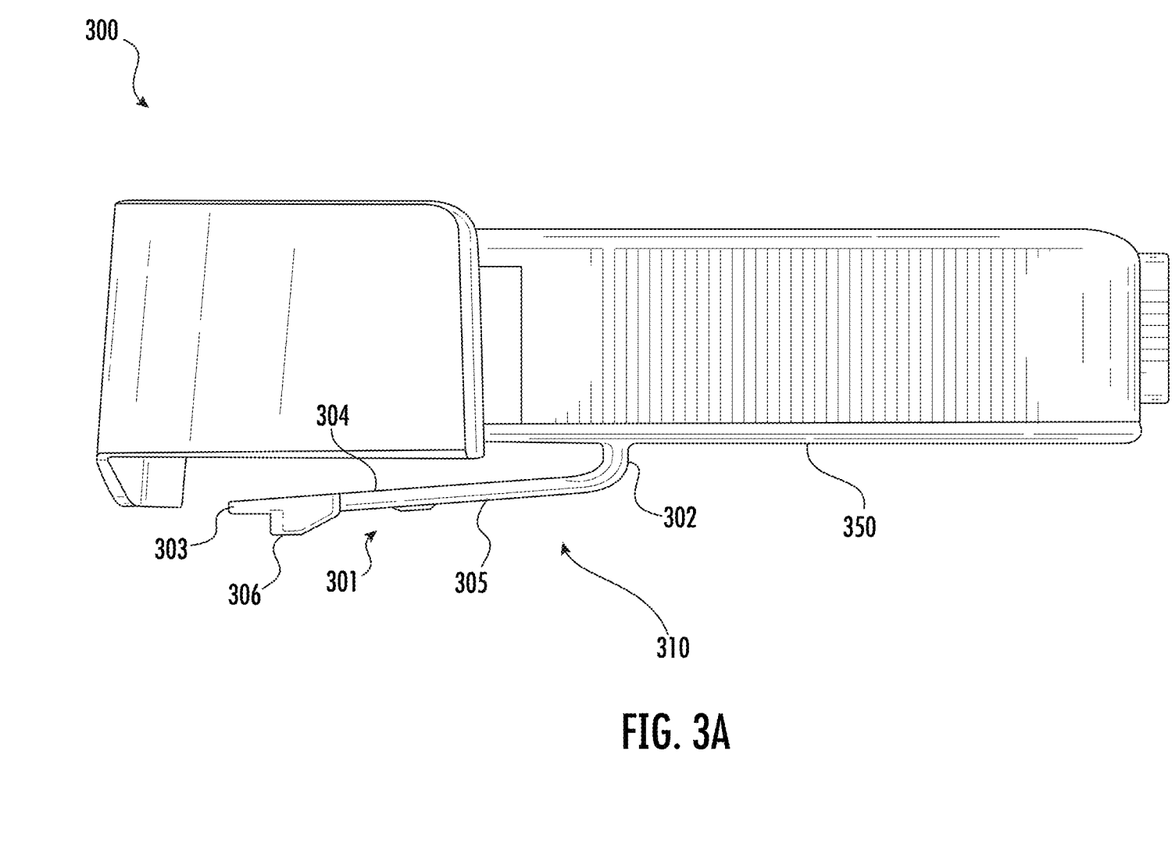
FIG. 3A illustrates a perspective side view of an example removable battery pack with a latch mechanism in accordance with various aspects and embodiments of the subject disclosure described herein.
Figure 3B:
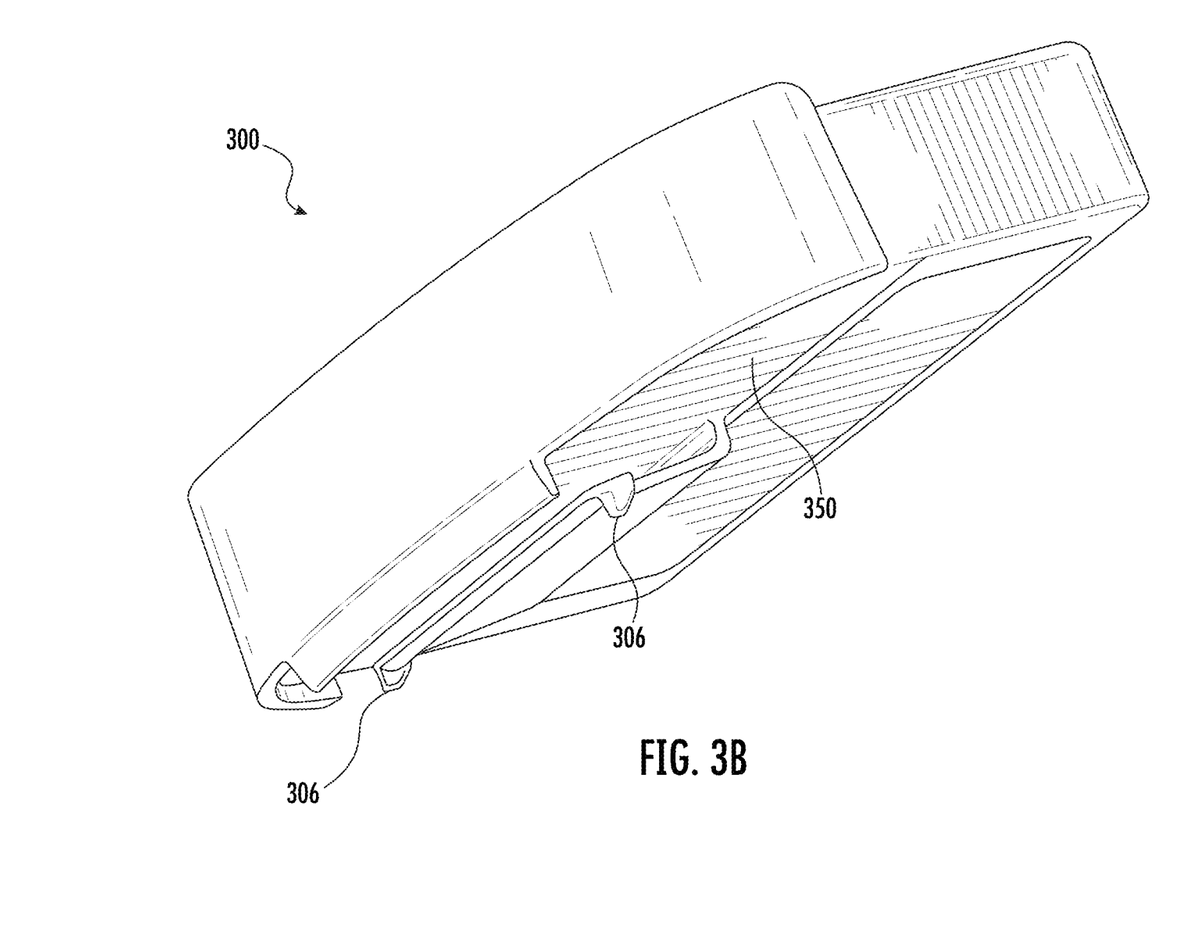
FIG. 3B illustrates a bottom front perspective view of an example removable battery pack with a latch mechanism in accordance with various aspects and embodiments of the subject disclosure described herein.
Figure 3C:
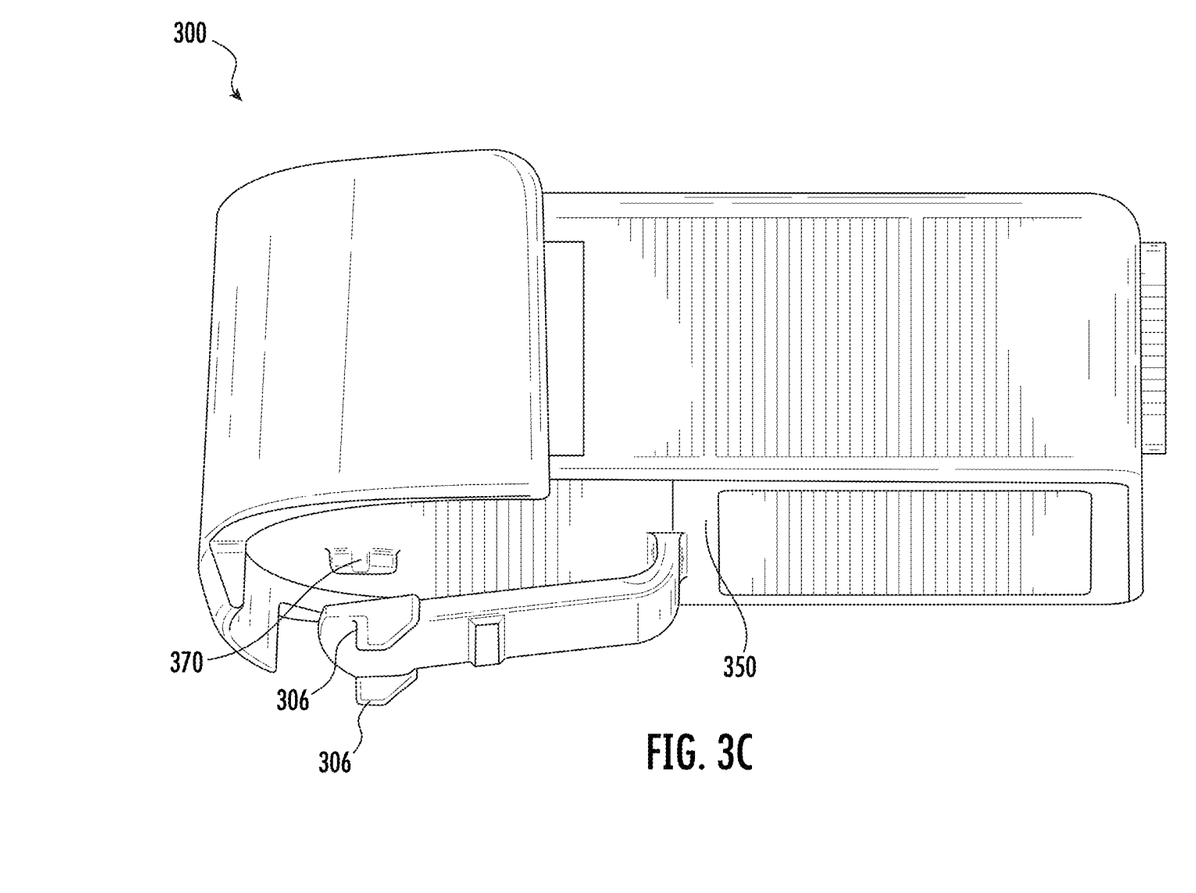
FIG. 3C illustrates a bottom side perspective view an example removable battery pack with a latch mechanism in accordance with various aspects and embodiments of the subject disclosure described herein.

FIGS. 3A-3C illustrate an example removable battery pack 300 with an example latch mechanism 306, 310 in accordance with various embodiments of the subject disclosure described herein. Specifically, FIG. 3A depicts a perspective side view, FIG. 3B depicts a bottom front perspective view, and FIG. 3C depicts a bottom side perspective view of the removable battery pack 300 with an example latch mechanism 306, 310 extending downward from an outer housing 350 of the removable battery pack 300. As described above, the latch mechanism 306, 310 may be configured for use with a battery enclosure or compartment 200 as illustrated in FIGS. 1-2.

With reference to FIG. 3A, as shown, the flexible latch 310 of the latch mechanism 306, 310 may include a main body 301. The main body 301 of the flexible latch 310 may define a first, proximal end 302 and a second, distal end 303, wherein the proximal end 302 of the flexible latch 310 is disposed proximate to and extending from the outer housing 350 of a removable battery pack 300. In this regard, in some embodiments, the proximal end 302 may define a latch base of the flexible latch 310. In some embodiments, the latch base is operable to attach the main body 301 of the flexible latch 310 to the outer housing 350 of the removable battery pack 300.

With continued reference to FIG. 3A, in some embodiments, the flexible latch 310 may further define an inner surface 304, the inner surface 304 facing the outer housing 350 of the removable battery pack 300. The flexible latch 310 may further define an opposing outer surface 305 of the flexible latch 310, the opposing outer surface 305 facing outwardly and designed to make contact with an inner surface of the battery enclosure or compartment 200 in an instance when the removable battery pack 300 is inserted into the battery enclosure or compartment 200.

With reference to FIGS. 3A-3C, in some embodiments, a portion of the opposing outer surface 305 of the flexible latch 310 may further define one or more locking tabs 306. In some embodiments, the one or more locking tabs 306 may protrude outwardly from the outer surface 305 of the flexible latch 310. Still in certain embodiments, the one or more locking tabs 306 are disposed proximate to the distal end 303 of the flexible latch 310. While illustrated herein with a locking tab 306 located at each edge of the outer surface 305 at the distal end 303 of the flexible latch 310 (e.g., such as depicted in FIGS. 3B and 3C), the present disclosure contemplates that the respective locking tabs 306 may be located at any position along the distal end 303 of the flexible latch 310.

The locking tabs 306 may be engageable with one or more engaging slots 205 operatively positioned within the battery enclosure 200 (e.g., as depicted in FIG. 2). In some embodiments, the receipt of the one or more locking tabs 306 of the flexible latch 310 in the one or more engaging slots 205 of the battery enclosure 200 helps to secure the removable battery pack 300 within the battery enclosure 200 and restricts or prevents sudden or unintended disengagement of the removable battery pack 300 during normal operating conditions, as described in detail below with respect to FIGS. 5A-5C. It should also be appreciated that while two locking tabs 306 are depicted, any suitable number of locking tabs 306 (e.g., and corresponding engaging slots 205 as in FIG. 2) may be utilized according to the present disclosure.

With reference to FIG. 3C, in some embodiments, the outer housing 350 of the removable battery pack 300 may include a stopper projection 370 operatively positioned on the bottom portion or bottom surface of the removable battery pack 300 to operably limit compression of the flexible latch 310 or otherwise prevent the flexible latch 310 from overextension. Said differently, the stopper projection 370 is positioned on the outer housing 350 to restrict the flexible latch 310 from being overextended or compressed beyond a threshold angle. For example, when a user depresses or engages the distal end 303 of the flexible latch 310 close to the outer housing 350 in order to disengage the locking tabs 306 from the engaging slots 205 of the battery enclosure or compartment 200 and remove the removable battery pack 300 from the battery enclosure or compartment 200, as described in detail below with respect to FIGS. 1, 2, and 5C, the stopper projection 370 may operate to prevent such overextension. The stopper projection 370 may be fixed to the outer housing 350 of the removable battery pack 300 via fasteners or more preferably, formed as part of an integral, one piece construction with the flexible latch 310 and at least a portion of the outer housing 350.

Figure 4:
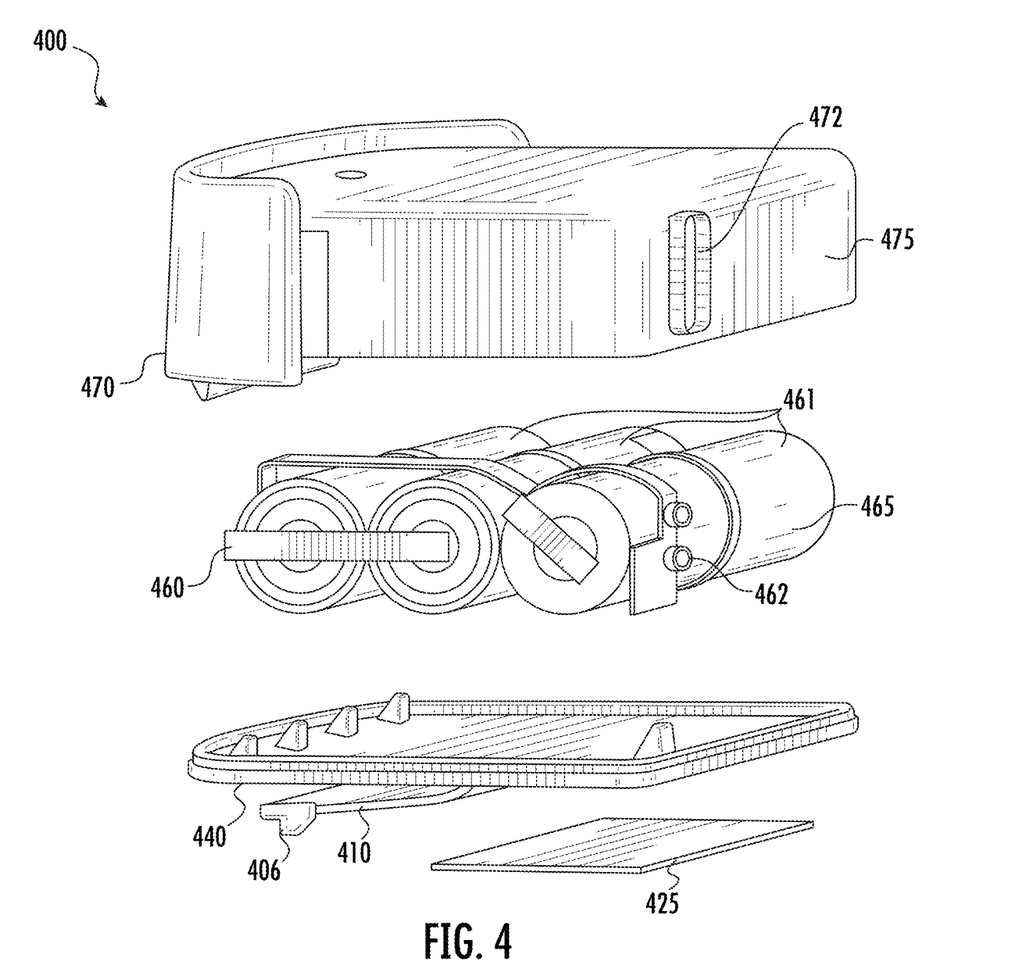
FIG. 4 illustrates an exploded schematic view of an example removable battery pack with a latch mechanism in accordance with various aspects and embodiments of the subject disclosure described herein.

With reference to FIG. 4, an exploded view of a removable battery pack 400 with an example latch mechanism 406, 410 is illustrated. As shown, the removable battery pack includes an upper portion 470 and a bottom portion 440, the upper portion 470 and the bottom portion 440 forming the outer housing 350 within which a battery assembly 460 is disposed. The battery assembly 460 includes one or more batteries 461 (e.g., three batteries as depicted in FIG. 4) which are electrically and, in some instances, physically connected to each other. A battery terminal 462 is disposed at the rear end 465 of the battery assembly 460 such that the battery terminal 462 electrically engages with a power connection 472 defined in the rear end 475 of the outer housing 350 of the removable battery pack 400. When the removable battery pack 400 is inserted in the battery enclosure or compartment 200, the rear end 475 of the removable battery pack 400 is inward facing, situated completely within the battery enclosure or compartment 200 such that the rear end 475 of the removable battery pack 400 is not visible. The removable battery pack 400 is configured to supply power to the PAPR 150 such that once inserted in the battery enclosure or compartment 200, the power connection 472 of the removable battery pack 400 provides an electrical connection between the removable battery pack 400 and a corresponding receiving connection (not depicted) disposed within the battery enclosure or compartment 200.

With continued reference to FIG. 4, an example flexible latch 410 may be integrally formed as part of, and extending from, the bottom portion 440 of the outer housing of the removable battery pack 400. It should be appreciated that while illustrated as a one-piece construction, the present disclosure contemplates that the flexible latch 410 may be formed separately and mounted on the bottom portion 440 of the outer housing of the removable battery pack 400. It should be also appreciated that while illustrated as extending from a bottom portion 440 of the outer housing of the removable battery pack 400, the present disclosure contemplates that the flexible latch 410 may be disposed in any suitable position that corresponds to a flexible latch receiving portion or latch-receiving void or cutout 201 of a battery enclosure or compartment 200.

With continued reference to FIG. 4, in some embodiments, a label 425 may be applied to the exterior surface of the removable battery pack 400 to provide any of a variety of information or data to a user. The label 425 may be applied to any suitable exterior surface of the removable battery pack 400. As depicted in FIG. 4, the label 425 is applied to the bottom portion 440 of the outer housing of the removable battery pack 400. The label 425 may be of a variety of shapes and sizes and may use a variety of adhesive types corresponding to the receiving exterior surface of the removable battery pack 400.

Figure 5A:
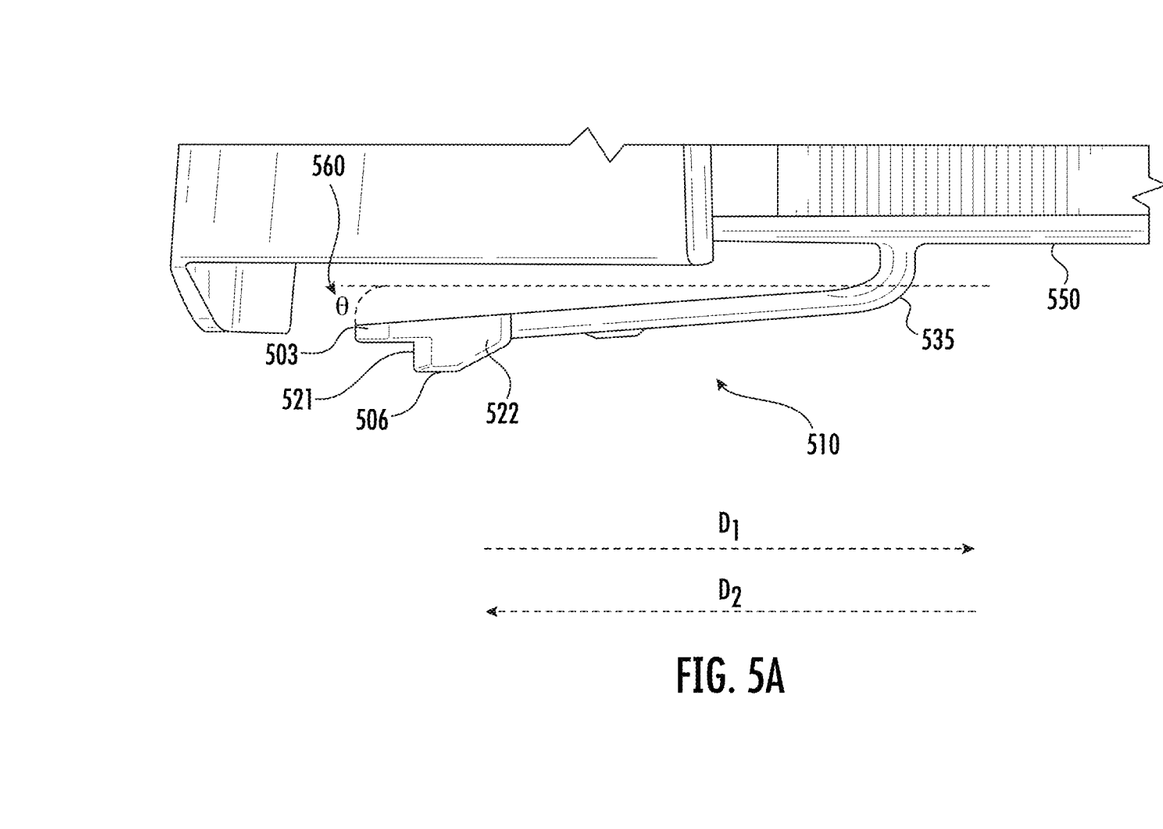
FIG. 5A illustrates example locking tabs and an example flexible latch in a first open configuration in accordance with various aspects and embodiments of the subject disclosure described herein.
Figure 5B:
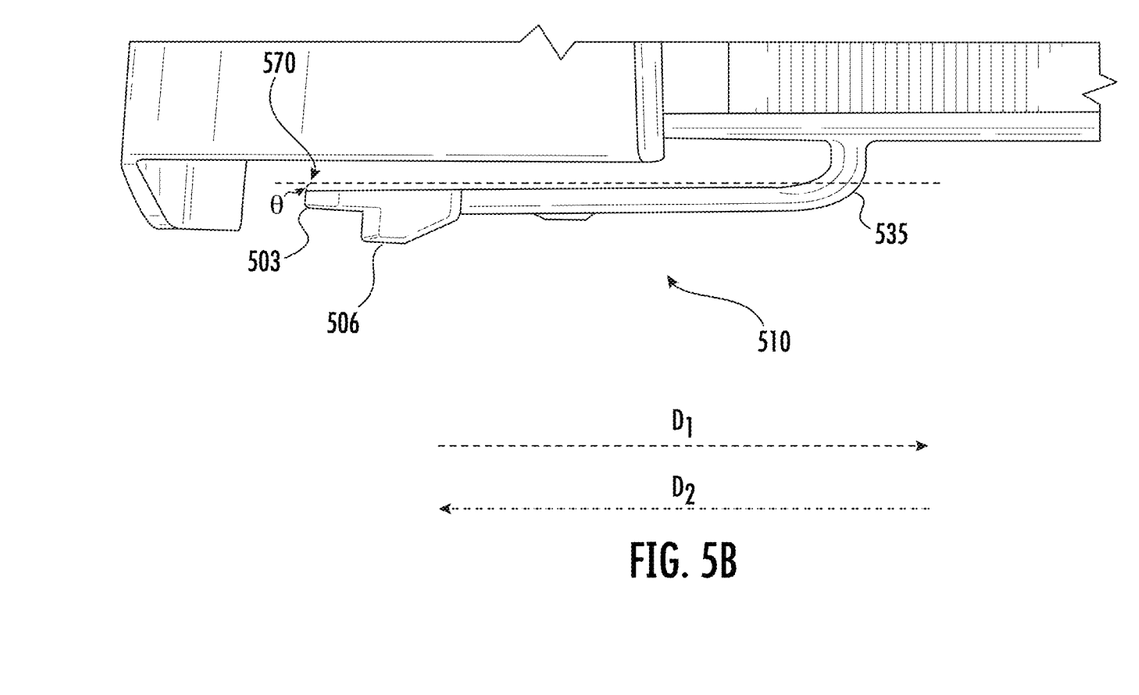
FIG. 5B illustrates an example flexible latch in a second compressed configuration in accordance with various aspects and embodiments of the subject disclosure described herein.
Figure 5C:
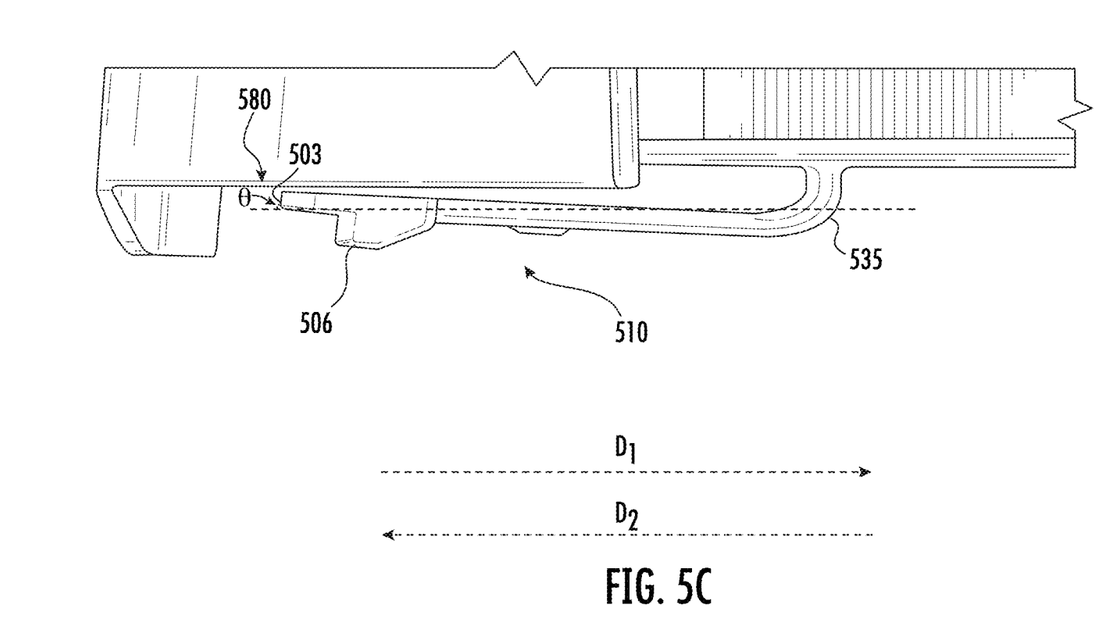
FIG. 5C illustrates an example flexible latch in a third compressed configuration in accordance with various aspects and embodiments of the subject disclosure described herein.

With reference to FIGS. 5A-5C, in some embodiments, the flexible latch 510 may extend from the outer housing 550 of the removable battery pack at various angles in relation to the outer housing 550. Said differently, the flexible latch 510 is attached at the outer housing 550 of the removable battery pack such that an angle $\theta$ is formed between the flexible latch 510 and the outer housing 550. In some embodiments, the angle $\theta$ varies in response to the application of pressure to the flexible latch 510 as described in detail below. In some embodiments, the angle $\theta$ is defined at the junction formed directly between the flexible latch 510 and outer housing 550 of the removable battery pack. With continued reference to FIGS. 5A-5C, in other embodiments, the flexible latch 510 may comprise an arcuate or curved portion 535 disposed proximate to the proximal end 302 or the latch base of the flexible latch 510 such that the angle $\theta$ is defined as the angle formed between an axis extending through the distal end 503 of the flexible latch 510 and an axis that is parallel with an axis defined by the outer housing 550 that intersects with the arcuate or curved portion 535. For example, in some embodiments, the axis that is parallel with an axis defined by the outer housing 550 that intersects with the arcuate or curved portion 535 is depicted by the dashed line in FIGS. 5A-5C. Such operatively disposed arcuate or curved portion 535 may operate as a pivot point, allowing the flexible latch 510 (e.g., the distal end 503) sufficient space to deform between at least the first open configuration, second compressed configuration, and the third compressed configuration described with respect to FIGS. 5A-5C.

FIG. 5A depicts a side perspective view of an example flexible latch 510 in a first open configuration in comparison to the outer housing 550 of the removable battery pack. In FIG. 5A, the first open configuration is defined by a first angle θ 560 in an instance wherein the distal end 503 of the flexible latch 510 is not subjected to any external stress or force by a user or the battery enclosure 200. The first angle θ 560 as defined between an axis extending through the distal end 503 of the flexible latch 510 and the axis that is parallel with the axis defined by the outer housing 550 that intersects with the arcuate or curved portion 535 (e.g., such as depicted by the dashed line in FIG. 5A) of the outer housing 550 formed at is a positive acute angle in the example embodiment depicted in FIG. 5A. With reference to angle θ, the angle θ is at its maximum in the first open configuration as depicted in FIG. 5A. In some embodiments, the first angle θ 560 is a positive acute angle.

FIG. 5B depicts a side perspective view of an example flexible latch 510 in a second compressed configuration in comparison to the outer housing 550 of the removable battery pack. In some embodiments, the distal end 503 of the flexible latch 510 may extend from the outer housing 550 at a second angle θ 570 in relation to the outer housing 550. With reference to FIG. 5B, the second angle θ 570 is defined between the axis extending through the distal end 503 of the flexible latch 510 and the axis that is parallel with the axis defined by the outer housing 550 that interacts with the arcuate or curved portion 535 (e.g., such as depicted by the dashed line in FIG. 5B). In some embodiments, the second angle θ 570 may be a smaller, positive acute angle as compared to the first angle θ 570. In other embodiments, the second angle θ 570 may be approximately 0° or equal to 0° such that the distal end 503 and the main body of the flexible latch 510 is substantially parallel to the bottom portion of the outer housing 550. In still other embodiments, the second angle θ 570 may be a negative acute angle. This second angle θ 570 defines the second compressed configuration in an instance wherein sufficient pressure is applied to the distal end 503 of the flexible latch 510, such that at least the distal end 503 of the flexible latch 510 is temporarily displaced while being inserted or after being completely inserted into the battery enclosure 200. In some embodiments, the flexible latch 510 is configured to exert an outwardly directed pressure while in the second compressed configuration. In such embodiments, the outwardly directed pressure of the flexible latch 510 biases the removable battery pack 100, 300 in a secured position within the battery enclosure or compartment 200, helping to restrict or prevent the unintended disengagement of the removable battery pack 100, 300 during normal operating conditions.

FIG. 5C depicts a side perspective view of an example flexible latch 510 in a third compressed configuration in comparison to the outer housing 550 of the removable battery pack. In some embodiments, the distal end 503 of the flexible latch 510 extends from the outer housing 550 at a third angle θ 580 in relation to the outer housing 550. With reference to FIG. 5C, the third angle θ 580 is defined between the axis extending through the distal end 503 of the flexible latch 510 and the axis that is parallel with the axis defined by the outer housing 550 that interacts with the arcuate or curved portion 535 (e.g., such as depicted by the dashed line in FIG. 5C). In some embodiments, the angle θ is decreased even more in the third compressed configuration such that the third angle θ 580 is a smaller, positive acute angle as compared to the first and second angles θ 570, 580. In other embodiments, the third angle θ 580 may be approximately 0° or equal to 0° such that the distal end 503 and the main body of the flexible latch 510 is substantially parallel to the bottom portion of the outer housing 550. In still other embodiments, as depicted in FIG. 5C, the third angle θ 580 corresponding to the third compressed configuration may be less than 0°, forming a negative acute angle in relation to the parallel axis extending from the arcuate or curved portion 535 of the flexible latch 510. This third angle θ 580 may correspond to an instance wherein sufficient pressure is applied to the distal end 503 of the flexible latch 510 to disengage the locking tabs 506 from the engaging slots 205 for removal of the battery pack 500, which is described in detail below with respect to FIGS. 1, 2, and 5C.

With reference to FIGS. 1, 2, and 5A, the one or more locking tabs 506 may be configured so as to prevent the disengagement of the locking tabs 506 from the one or more engaging slots 205 of the battery enclosure. As shown in FIG. 5A, the first edge 522, or leading edge 522, of the locking tab 506 is illustrated as extending at an obtuse angle from the outer surface of the flexible latch 350. In this way, as the leading edge 522 of the locking tab 506 engages the battery enclosure or compartment 200, the insertion of the removable battery pack 100 into the battery enclosure or compartment 200 is not hindered. The second, opposing edge 521, or trailing edge, is illustrated as extending perpendicularly from the outer surface of the flexible latch 510. In this way, once the removable battery pack 100 is fully inserted in the battery enclosure 200 and the locking tabs 506 are engaged with the engaging slots 205 of the battery enclosure 200, the second, opposing edge 521 of the locking tab 506 helps to prevent the removable battery pack 100 from withdrawing from the battery enclosure or compartment 200 under normal operating conditions. Said differently, the asymmetrical shape of the locking tab 506 is such that the locking tab 506 (and removable battery pack 100) may be inserted in a first direction $D_1$ into the battery enclosure 200 as depicted in FIGS. 1 and 5A, but movement of the locking tab 506 (and the removable battery pack 100) in a second opposite direction $D_2$ is prevented.

With reference to FIGS. 1, 2, and 5B-5C, the removable battery pack 100 may be removed from the battery enclosure or compartment 200 when necessary. Said differently, the flexible latch 510 may be moveable by a user from a position (e.g., a second compressed configuration as depicted in FIG. 5B) in which the locking tabs 506 engage the engaging slots 205 of the battery enclosure or compartment 200 to prevent disengagement of the removable battery pack 100 to a disengaging position (e.g., a third compressed configuration as depicted in FIG. 5C), in which the locking tabs 506 are no longer engaged with the engaging slots 205 of the battery enclosure or compartment 200. Upon the application of sufficient pressure to the distal end 503 of the flexible latch 510 in order to disengage the locking tabs 506 from the engaging slots 205, the angle θ is decreased, corresponding to the third compressed configuration. In order to remove the removable battery pack 100, the user depresses the flexible latch 510 by accessing the distal end 503 of the flexible latch 510 through the latch-receiving void or cutout 201 of the battery enclosure 200, pushing the flexible latch 510 closer to or toward the outer housing 550 of the removable battery pack 100 and applying sufficient force to disengage the one or more locking tabs 506 from the one or more engaging slots 205 of the battery enclosure or compartment 200 of the PAPR 150, and then pulling the removable battery pack 100 in direction D₂ to withdraw the removable battery pack 100 from the battery enclosure 200.

In some examples, the flexible latch 310, 410, 510 is constructed of a resilient material such that the flexible latch 310, 410, 510 may be deformed from a first open configuration into one or more compressed configurations. For example, the flexible latch 310, 410, 510 is deformable or displaced from a first open configuration to a second compressed configuration upon complete insertion into the battery enclosure or compartment 200. In still further embodiments, the flexible latch 310, 410, 510 is operable such that it returns to the first open configuration upon withdrawal from the battery enclosure 200. Said differently, the resilient material allows for temporary deformation of the flexible latch 310, 410, 510 under stress but does not irreversibly deform the flexible latch 310, 410, 510.

The resilient material provides sufficient flexibility to allow the flexible latch 310, 410, 510 to deform upon insertion into the battery enclosure 200 as the battery enclosure 200 exerts pressure on the flexible latch 310, 410, 510 and reform to its open configuration upon withdrawal of the removable battery pack 100 from the battery enclosure 200, while also providing sufficient stiffness to reliably secure the removable battery pack 100 while retained within the battery enclosure 200 during normal operating use. While a variety of different materials may be suitable, in certain embodiments the flexible latch 310, 410, 510 is formed from a polymer material. In still certain embodiments, the flexible latch 310, 410, 510 is formed from a polycarbonate/acrylonitrile butadiene styrene (PC+ABS) blend.

In some examples, the outer housing 350, 440, 470, 550 of the removable battery pack 100 may be made from the same material as the flexible latch 310, 410, 510, or the outer housing 350, 440, 470, 550 could be formed of a different material. Preferably, however, the flexible latch 310, 410, 510 and at least a portion of the outer housing 350, 440, 470, 550 of the removable battery pack 100 are made of the same material. More preferably, the flexible latch 310, 410, 510 and at least a portion of the outer housing 350, 440, 470, 550 may be formed as an integral, one piece member. Most preferably, the flexible latch 310, 410, 510 is formed during injection molding of at least a portion of the outer housing 350, 440, 470, 550 of the removable battery pack 100. For example, the bottom portion 440 of the outer housing and the flexible latch 410 illustrated in FIG. 4 are formed as an integral, one piece member using injection molding. It should be appreciated that while illustrated as a one-piece construction, the present disclosure contemplates that any suitable modular or multi-piece construction may be utilized.

Figure 6:
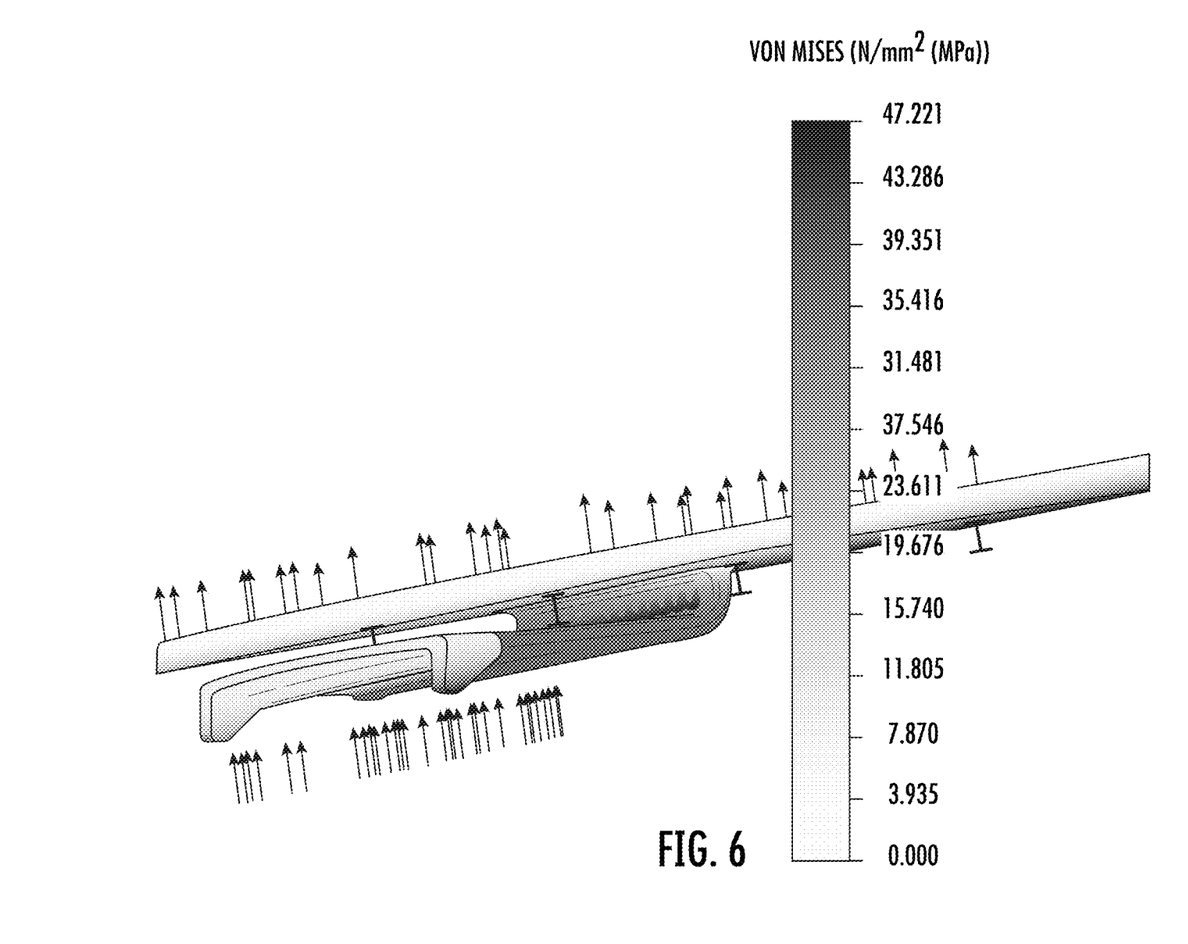
FIG. 6 illustrates stress readings from an exemplary flexible latch in accordance with various aspects and embodiments of the subject disclosure described herein.
Figure 7:
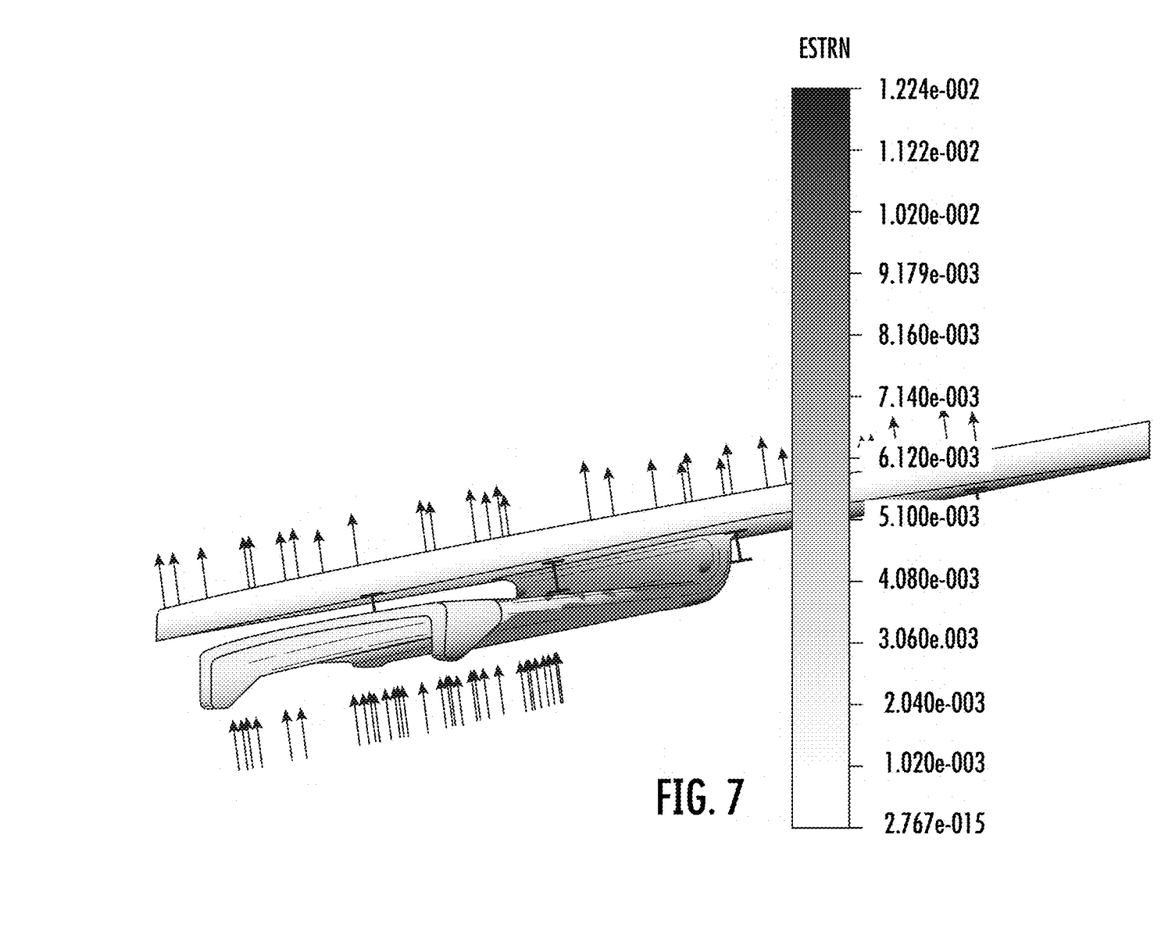
FIG. 7 illustrates strain readings from an exemplary flexible latch in accordance with various aspects and embodiments of the subject disclosure described herein.

Exemplary flexible latches 310, 410, 510 in accordance with various embodiments described herein are illustrated in FIGS. 6 and 7. Specifically, without being limited hereto, FIGS. 6 and 7 illustrate stress and strain readings from exemplary experimental flexible latches 310, 410, 510 elucidating the durableness and resiliency of various embodiments described herein. FIG. 6 illustrates the stress readings measured in various locations of a flexible latch formed of PC+ABS material upon the application of 40N of pressure. As depicted, the stress reading on the central portion of the arcuate portion of the flexible latch is approximately 47 N/mm². Thus, in a flexible latch formed of PC+ABS material, the arcuate portion of the flexible latch can withstand more than 10,000 cycles at a pressure of 40N according to the SN curve for PC+ABS. FIG. 7 illustrates the strain readings measured in various locations of the flexible latch 310, 410, 510 depicted in FIG. 6. As depicted, the strain reading on the central portion of the arcuate portion of the flexible latch is approximately 1%, indicating little deformation of the flexible latch.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A latch mechanism for securing a removable battery pack within a battery enclosure of a powered air purifying respirator (PAPR), the latch mechanism comprising:

a flexible latch disposed on an outer housing of the removable battery pack, the flexible latch defining an inner surface facing the outer housing and an opposing outer surface, wherein a portion of the opposing outer surface of the flexible latch defines one or more locking tabs that are engageable with one or more engaging slots operatively positioned within the battery enclosure, and wherein the flexible latch is deformable from a first open configuration to a second compressed configuration upon insertion into the battery enclosure.

2. The latch mechanism of claim 1, wherein the one or more locking tabs protrude outwardly from the opposing outer surface of the flexible latch.

3. The latch mechanism of claim 1, wherein the flexible latch further defines a proximal end and a distal end, the proximal end disposed proximate to and extending from the outer housing of the removable battery pack such that the proximal end defines a latch base.

4. The latch mechanism of claim 3, wherein the one or more locking tabs are disposed proximate to the distal end of the flexible latch.

5. The latch mechanism of claim 3, wherein the flexible latch comprises an arcuate portion proximate to the latch base.

6. The latch mechanism of claim 1, wherein the flexible latch extends from the outer housing at a first angle in relation to the outer housing, the first angle defining the first open configuration.

7. The latch mechanism of claim 6, wherein the first angle is an acute angle.

8. The latch mechanism of claim 6, wherein the flexible latch extends from the outer housing at a second angle in relation to the outer housing, wherein the first and second angles are different and the second angle defines the second compressed configuration.

9. The latch mechanism of claim 1, wherein the flexible latch is configured to exert an outwardly directed pressure in the second compressed configuration.

10. The latch mechanism of claim 1, wherein the flexible latch is integrally formed with at least a portion of the outer housing of the removable battery pack.

11. The latch mechanism of claim 1, wherein the flexible latch is formed during injection molding of at least a bottom portion of the outer housing of the removable battery pack.

12. The latch mechanism of claim 1, wherein the flexible latch is formed of a polymer material.

13. The latch mechanism of claim 12, wherein the flexible latch is formed of a polycarbonate/acrylonitrile butadiene styrene blend.

14. The latch mechanism of claim 1, wherein the one or more locking tabs each have a first edge extending at an acute angle from the outer surface of the flexible latch and a second, opposing edge extending perpendicularly from the outer surface of the flexible latch.

15. The latch mechanism of claim 1, wherein at least one of the one or more locking tabs has a locking edge, such that engagement of the locking tab with the one or more engaging slots prevents disengagement of the removable battery pack from the battery enclosure.

16. The latch mechanism of claim 1, wherein the flexible latch is operable to return to the first open configuration upon withdrawal from the battery enclosure.

17. The latch mechanism of claim 1, wherein the flexible latch is deformable from the second compressed configuration to a third compressed position.

18. The latch mechanism of claim 17, wherein the flexible latch is operable to deform from the second compressed configuration to the third compressed position upon application of a force sufficient to disengage the one or more locking tabs from the one or more engaging slots of the PAPR.

19. The latch mechanism of claim 1, wherein the outer housing of the removable battery pack comprises a stopper projection operatively positioned to prevent the flexible latch from overextension.

20. A removable battery pack, the removable battery pack comprising:
    a battery assembly;
    an outer housing; and
    a flexible latch, the flexible latch comprising:
        a main body operable to deform from a first open configuration to a second compressed configuration upon insertion into a corresponding battery compartment,
        a latch base defined by a first end of the main body, the latch base operable to attach the main body of the flexible latch to the outer housing of the removable battery pack, and
        a latch end comprising one or more locking tabs, the one or more locking tabs operable to engage with one or more engaging slots operatively positioned within the corresponding battery compartment, wherein an angle $\theta$ is defined at least in part by an axis of the flexible latch, the angle $\theta$ varying in response to application of pressure to the flexible latch.

* * * * *